US00PP09464P

United States Patent [19]

Challet

[11] Patent Number: Plant 9,464

[45] Date of Patent: Mar. 5, 1996

[54] CHRYSANTHEMUM PLANT NAMED 'CHAPLOU'

[75] Inventor: Jean-Pierre Challet, Lafayette, Calif.

[73] Assignee: Selection New Plant Sarl, Le Cannet Des Maures, France

[21] Appl. No.: 273,992

[22] Filed: Jul. 12, 1994

[51] Int. Cl.[6] ..... A01H 5/00

[52] U.S. Cl. ..... Plt./82.3

[58] Field of Search ..... Plt./74.1, 82.5, Plt./82.3, 82

[56] References Cited

U.S. PATENT DOCUMENTS

| | | | |
|---|---|---|---|
| P.P. 4,722 | 5/1981 | Meek et al. | Plt./82.5 |
| P.P. 6,944 | 7/1989 | VandenBerg | Plt./82.5 |
| P.P. 7,447 | 2/1991 | VandenBerg | Plt./82 |
| 4,616,099 | 10/1986 | Sparkes | 47/58 |

OTHER PUBLICATIONS

Gosling, ed., 1979, "The Chrysanthemum Manual–6th edition," The National Chrysanthemum Society, Essex Telegraph Press, Ltd., Colchester, pp. 329–336.

Gupta, et al., 1978, "Mutation breeding of Chrysanthemum, II. Deketion of gamma ray induced Sometic mutation in vMz", J. Nuclear Agrio. Biol. 7(2):50–54.

Broertjes, et al., 1978, "Application of Mutation Breeding Methods In The Improvement of Vegetatively Propagated Crops", Elserier Sci. Pub. Co., New York, pp. 162–175.

Dowrick, et al., 1966, "The inductiopn of mutation in Chrysanthemum using X and gamma radiation", Euphytica 15:204–210.

Broertjes, 1966, "Mutation breeding of Chrysanthemums", Euphytica, 15:156–162.

Datta, 1991, "Evaluation of recurrent irradiaton on vegetatively propapated ornamentals: Chrysanthemum", J. Nuclear Agric. Biol., 20(2):81–86.

Banerji, et al., 1990, "Induction of somatic mutation in Chrysanthemum cuttivar 'Anupam'", J. Nuclear Agric. Biol., 19:252–256.

Das, et al., 1977, "Improvement of some vegetatively propagated ornamentals by gamma radiation", Indian J. Hort., 34(2):169–174.

*Primary Examiner*—Howard J. Looker

*Attorney, Agent, or Firm*—Burns, Doane, Swecker & Mathis

[57] ABSTRACT

A new and distinct chrysanthemum cultivar named 'Chaplou' is provided. The new cultivar is a mutation of the 'Chakara' cultivar (U.S. Plant. Pat. application Ser. No. 8/273,994, filed Jul. 12, 1994) that was created through gamma irradiation. Attractive red bronze anemone blossoms are formed in profusion (as illustrated). The response period of the flowers is approximately eight weeks. Recurrent flower production throughout the year is possible. The plant possesses soft and thin stems, forms attractive leaves, and commonly assumes a height of approximately 30 to 35 cm. The new cultivar is particularly suited for use in the production of a decorative pot chrysanthemum. No growth regular is required to achieve the short plant height.

3 Drawing Sheets

SUMMARY OF THE INVENTION

The present invention comprises a new and distinct cultivar of Chrysanthemum, botanically known as *Dendranthema grandiflora,* and hereinafter is referred to by the cultivar name 'Chaploup'.

The new cultivar of the present invention was created through the gamma irradiation of the 'Chakara' cultivar (U.S. Plant patent application Ser. No. 08/273,992, filed Jul. 12, 1994). The parent 'Chakara' cultivar was formed by the crossing of the 'Fada' cultivar (non-patented in the United States) and the 'Domi' cultivar (non-patented in the United States) as described in my copending U.S. patent application.

During June 1988, at Saint Paul Lez Durance, France, groups of 1,000 rooted cuttings of the 'Chakara' cultivar having an age of two weeks were irradiated with gamma rays through the packing boxes at rates of 1.8, 2.5 and 3.0 Krads. Following irradiation the plants were shipped to Nuaille, Trementines, France, and planted in 4 liter pots, pinched, and grown outside until September, next grown in greenhouses, were not disbudded, and were carefully observed. It was found that most of the plants irradiated at a rate of 3.0 Krads died. Those plants that were irradiated at rate 2.5 Krads exhibited no growth following pinching and were discarded. Many different mutations were observed in the plants that were irradiated at a rate of 1.8 Krads. A single mutation that exhibits the characteristics of the 'Chaplou' cultivar was discovered among these plants. Also, a single cultivar that exhibits the characteristics of the 'Chaprila' cultivar (U.S. Plant patent application Ser. No. 08/274,001, filed Jul. 12, 1995) was discovered among the same groups of plants. It would have been impossible for a plant scientist to have predicted in advance that new cultivars having the combination of characteristics of the presently claimed 'Chaplou' cultivar and the sister 'Chaprila' cultivar could have been formed even if the parent 'Chakara' cultivar would have been available for such experimentation.

It was found that the new 'Chaplou' cultivar of the present invention:

(a) exhibits in profusion attractive large red bronze anemone blossoms, (b) exhibits a flower response period of approximately eight weeks, (c) is highly amenable to branching by pinching, (d) achieves a short plant height, and (e) is particularly suited for pot mum production on a recurrent basis throughout the year.

The new cultivar is intended for use primarily as a decorative pot anemone spray Chrysanthemum for growing indoors. However, the new cultivar can be grown outdoors at temperatures above freezing.

In the absence of debudding a profusion of blossoms form per stem (as illustrated). The new cultivar can also be grown as a disbud to form striking blooms. A greatly increased number of branches readily can be induced by pinching. The pinching of a cutting commonly produces 5 or more stems.

No growth regulator is required to produce the short plant height.

The new cultivar can be considered to be an October-flowering greenhouse variety with the natural flowering season commonly occurring in weeks 41 and 42 of the year. Attractive blossoms can be produced on a recurrent basis throughout the year with the indicated eight week response period. The blossoms commonly last approximately one and one-half weeks on the plant, and commonly less than one week when placed in a vase.

Night temperatures above approximately 23° C. will delay flowering. Night temperatures as low as 14° C. generally can be well tolerated, and night temperatures as low as 5° to 10° C. can be tolerated at the bud-cracking stage.

Asexual reproduction of the new cultivar by cuttings initially taken during 1991, as performed in Nuaille, Trementines, France, in a controlled environment has demonstrated that the characteristics of the new cultivar as herein described are firmly fixed and are retained through successive generations of asexual propagation.

'Chaplou' has not been observed under all possible environmental conditions to date. Accordingly, it is possible that the phenotype may vary somewhat with variations in the environment, such as temperature, light, day length, contact with pesticides and/or subjection to growth retardant treatments.

The 'Chaplou' cultivar of the present invention can be readily distinguished from its parent. More specifically, the 'Chaplou' cultivar exhibits a red bronze capitulum unlike the bright bronze capitulum of the 'Chakara' cultivar, a stem coloration of Yellow-Green Group 146D instead of Yellow-Green 144A for the 'Chakara' cultivar, anthocyanin coloration mainly at the nodes unlike the 'Chakara' cultivar, an angular stem cross section unlike the round stem cross section of the 'Chakara' cultivar, medium leaf serration unlike the medium to coarse leaf serration of the 'Chakara' cultivar, an upper leaf surface coloration of near Yellow-Green Group 144A but more green unlike the coloration of Green Group 137B to 137C coloration for the 'Chakara' cultivar, the absence of a claw in the base of the sinus between lateral leaf lobes unlike the 'Chakara' cultivar, a mucronate leaf apex unlike the cuspidate leaf apex of the 'Chakara' variety, a concave ray floret cross section unlike the generally flat ray floret cross section of the 'Chakara' cultivar, and a long day leaf count of approximately 15 to 19 unlike the 17 to 22 count commonly exhibited by the 'Chakara' cultivar.

Also, the 'Chaplou' cultivar of the present invention can be readily distinguished from its sister 'Chaprila' cultivar. More specifically, the 'Chaplou' cultivar exhibits a red bronze capitulum unlike the golden yellow capitulum of the 'Chaprila' cultivar, a stem coloration of Yellow-Green Group 146D instead of Yellow-Green Group 146C for the 'Chaprila' cultivar, anthocyanin coloration mainly at the nodes unlike the 'Chaprila' cultivar, a less coarse leaf serration that the 'Chaprila' cultivar, an upper leaf surface coloration of near Yellow-Green Group 144A but more green unlike the coloration between Green Group 137C and Yellow-Green Group 146B for the 'Chaprila' cultivar, an absence of a claw in the base of the sinus between lateral leaf lobes unlike the 'Chaprila' cultivar, converging margins of sinus between leaf lobes unlike the parallel margins of the 'Chaprila' cultivar, a concave ray floret cross section unlike the weakly convex ray floret cross section of the 'Chaprila' cultivar, and a long day leaf count of approximately 15 to 19 unlike the 17 to 19 count commonly exhibited by the 'Chaprila' cultivar.

The new 'Chalou' cultivar of the present invention is being marketed under the MARS trademark.

BRIEF DESCRIPTION OF THE PHOTOGRAPHS

The accompanying photographs were prepared during June, 1994, and show as nearly true as it is reasonably possible to make the same in color illustrations of this character, typical plants and plant parts of the new cultivar of the present invention. The plants were 13 weeks of age and were grown at Nuaille, Trementines, France, under standard greenhouse conditions which approximate those commonly utilized for the production of decorative pot mums. The plants had been pinched once and had not been disbudded. No growth regulant was utilized. Any labels shown in the photographs are 2.5 cm. in width and can be used for size comparisons.

DETAILED DESCRIPTION

Figure 1:
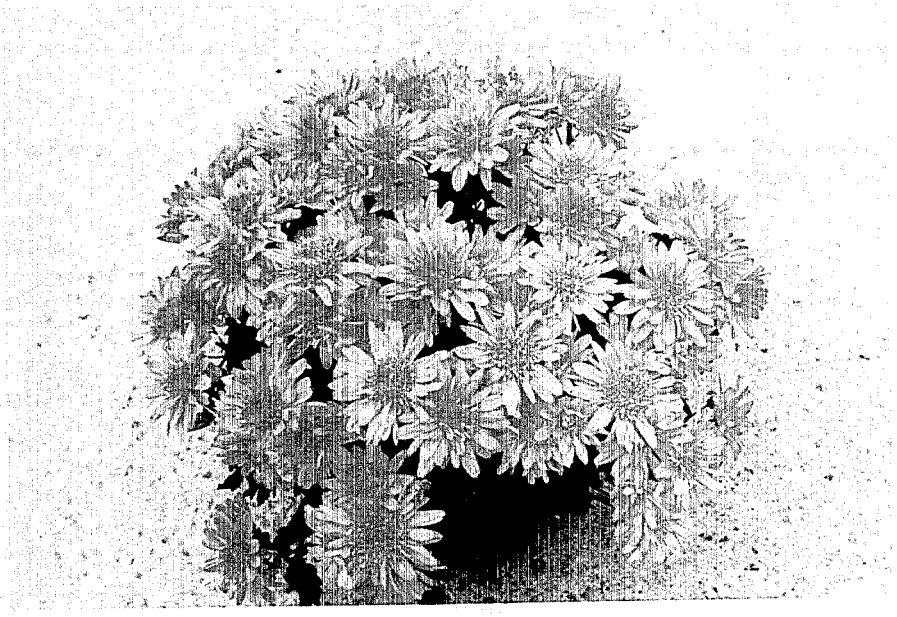
FIG. 1 illustrates typical specimens of the overall plant wherein three cuttings were placed in a 20 cm. pot. The red bronze anemone flowers, as well as the foliage, are apparent.
Figure 2:
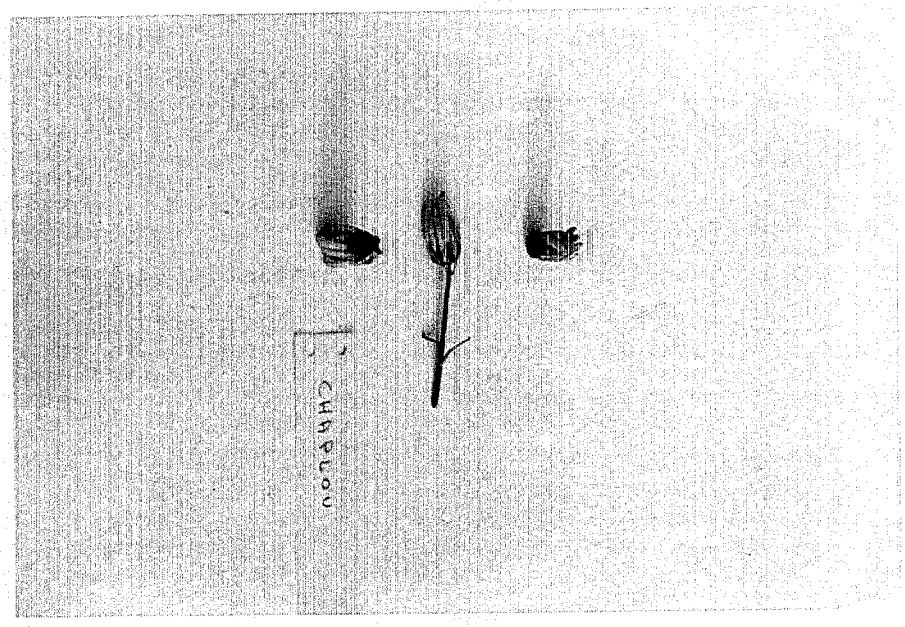
FIG. 2 illustrates from left to right, under, side, and upper views of largely unopened buds.
Figure 3:
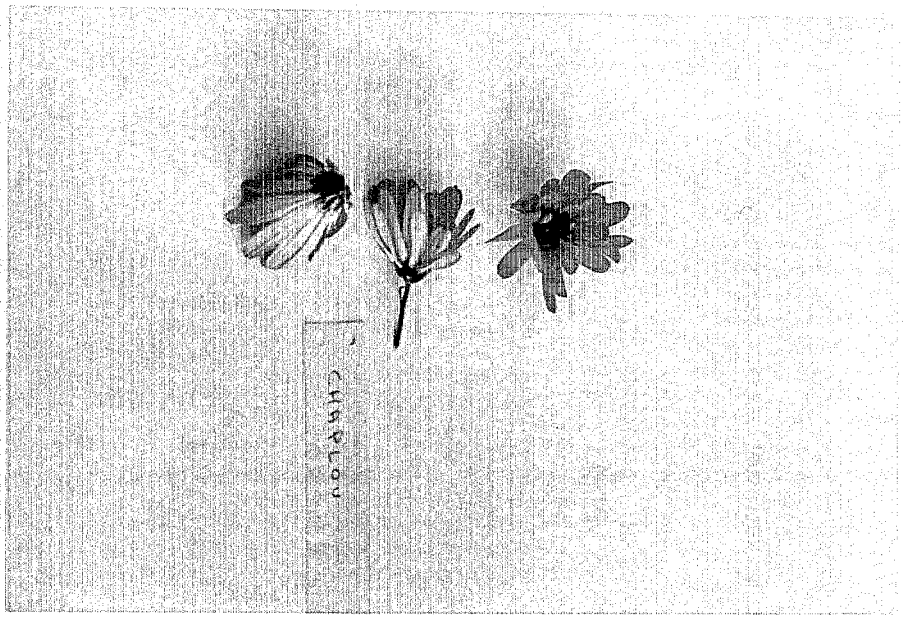
FIG. 3 illustrates from left to right, under, side, and upper views of flowers in the course of opening.
Figure 4:
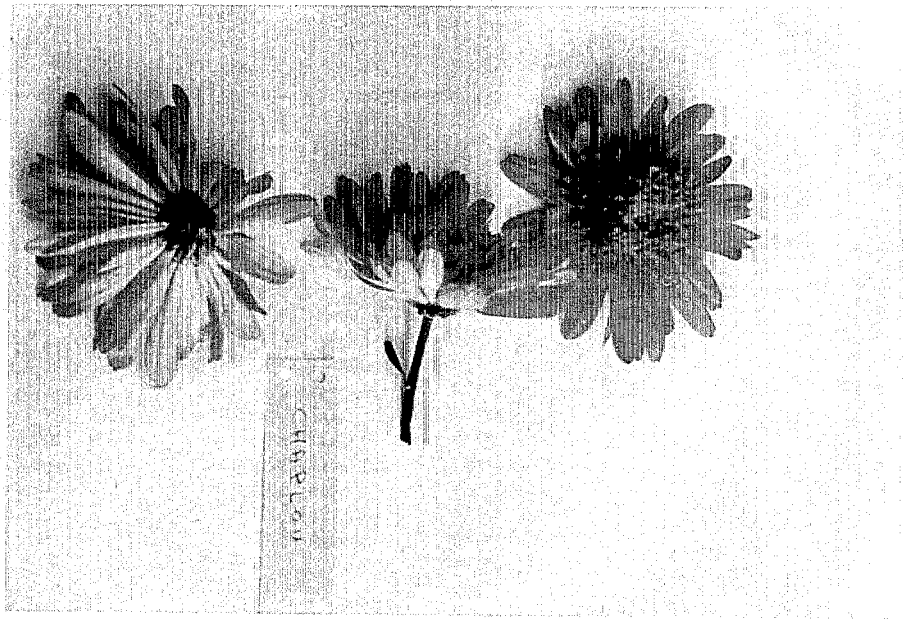
FIG. 4 illustrates from left to right, under, side, and upper views of the flowers in the course of opening. The darker coloration of the upper surfaces of the blossoms when immature is visible.
Figure 5:
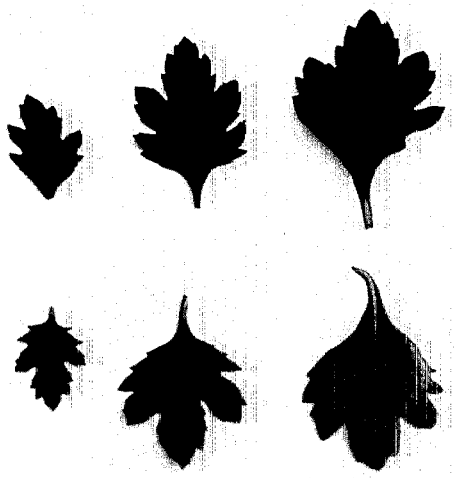
FIG. 5 illustrates at the top row the upper surfaces of typical leaves of various sizes, and at the bottom row the under surfaces of typical leaves of various sizes.

The chart used in the identification of colors described hereinafter is the R.H.S. Colour Chart of The Royal Horticultural Society, London, England. In some instances more common color terms are provided and are to be accorded their usual dictionary significance. The plants described were 13 weeks of age and were grown at Nuaille, Trementines, France, under standard greenhouse conditions which approximate those commonly utilized for the production of decorative pot mums.

Classification:

*Botanical.*—*Dendranthema gradiflora,* cv. 'Chaplou'.

*Commercial.*—Decorative pot mum.

INFLORESCENCE

A. Capitulum:

*Type.*—Anemone.

*Diameter across face.*—Medium, approximately 9 cm. on average when fully expanded.

*Frequency.*—Corymbiform, and blossoms form in profusion (as illustrated).

*Outside bud coloration.*—New Greyed-Red Group 182A but greyer.

B. Corolla of ray and disc florets:

*Disc florets.*—Petaloid, numerous, short, massed and clearly visible at all stages of flower head development, and commonly form a disc of approximately 2.5 cm. in diameter.

*General tonality.*—Red bronze capitulum that tends to fade somewhat as the blossoms fully mature.

*Color of disc florets.*—Before dehiscence, near Red Group 53A commonly with some yellow coloration near Yellow Group 1C at the extreme tip. At anther dehiscence, Red Group 46A with yellow near Yellow Group 4A at the extreme tip. After anther dehiscence, the inner surfaces are Red Group 46A with yellow at the extreme tip, and the outer surfaces are near Greyed-Orange Group 173A but more yellow.

*Color ray florets.*—The inner surfaces commonly are Orange-Red Group 34B with some deeper tints and with weak purple tones, and the outer surfaces commonly are near Greyed-Orange Group 172C but more yellow. The color is best when the plant is finished cool, since the plant generally does not well tolerate high levels of heat. The coloration tends to fade (as illustrated) as the blossoms mature.

*Configuration ray florets.*—Concave in cross section, rough in texture, generally straight, and possess dentated tips.

C. Reproductive organs:

*Androecium.*—Generally present with disc florets and absent in ray florets.

*Gynoecium.*—Generally present with most disc florets and with most ray florets.

*Pollen.*—Generally present in a relatively large quantity, and golden-yellow in coloration.

*Fragrance.*—Typical of Chrysanthemum.

PLANT

A. General apperance:

*Height.*—Short, and approximately 30 to 35 cm. in height on average at 10 weeks of age. The exact height is influenced by the growing conditions.

*Growth habit.*—Normal.

B. Foliage:

*Color (upper surface).*—Near Yellow-Green Group 144A but greener.

*Color (under surface).*—Generally slightly lighter green than upper surface.

*Long day leaf count.*—Approximately 15 to 19 leaves per typical stem in a long day crop before the bud occurs.

*Configuration.*—Very short and lobed (as illustrated).

*Texture.*—Fleshy.

*Serration.*—Medium.

*Shape of base.*—Asymmetric and occasionally truncated or rounded.

*Apex.*—Mucronate.

*Internode length.*—Very short.

*Stems.*—Thin, solf, angular in cross section, Yellow-Green Group 146D in coloration, and commonly with anthocyanin coloration mainly at the nodes.

*Claw in base of sinus beteen lateral lobes.*—Absent.

*Margins of sinus between lateral lobes.*—Converging.

I claim:

1. A new and distinct cultivar of Chrysanthemum plant named 'Chaplou', substantially as herein shown and described, which (a) exhibits in profusion attractive large red bronze anemone blossoms, (b) exhibits a flower response period of approximately eight weeks, (c) is highly amenable to branching by pinching, (d) achieves a short plant height, and (e) is particularly suited for pot mum production on a recurrent basis throughout the year.

* * * * *